(12) United States Patent
Click et al.

(10) Patent No.: US 9,579,138 B2
(45) Date of Patent: Feb. 28, 2017

(54) HIGH PRESSURE SURGICAL SYSTEM (71) Applicant: Kyphon SARL, Neuchatel (CH)

(72) Inventors: Bryan A. Click, Fremont, CA (US); Brian W. Donovan, San Jose, CA (US)

(73) Assignee: Kyphon SÀRL, Neuchâtel (CH)

(*) Notice: Subject to any disclaimer, the term of this patent is extended or adjusted under 35 U.S.C. 154(b) by 0 days.

(21) Appl. No.: 14/645,485

(22) Filed: Mar. 12, 2015

(65) Prior Publication Data
US 2015/0182274 A1 Jul. 2, 2015

Related U.S. Application Data (63) Continuation of application No. 12/512,929, filed on Jul. 30, 2009, now Pat. No. 9,005,209.

(51) Int. Cl.
A61B 17/56 (2006.01)
A61B 17/88 (2006.01)

(52) U.S. Cl.
CPC ................. A61B 17/8822 (2013.01)

(58) Field of Classification Search
CPC ........................ B05C 17/005–17/015
USPC ........ 606/92–94, 79, 80; 604/220, 221, 228, 604/223, 224
See application file for complete search history.

(56) References Cited

U.S. PATENT DOCUMENTS

| | | | | |
|---|---|---|---|---|
| 4,081,112 A * | 3/1978 | Chang | ................. | B05C 17/0123 222/391 |
| 4,262,822 A * | 4/1981 | Corte | ................. | B05C 17/0123 222/174 |
| 4,409,970 A * | 10/1983 | Carrel | ................. | A61F 13/041 602/40 |
| 4,432,753 A * | 2/1984 | Cassou | ................. | A61D 19/027 600/35 |
| 4,966,601 A | 10/1990 | Draenert | | |
| 4,973,334 A * | 11/1990 | Ziemann | ............. | A61B 17/8822 606/92 |
| 5,052,243 A * | 10/1991 | Tepic | ................. | A61B 17/3201 222/326 |
| 5,192,008 A * | 3/1993 | Hwan | ................. | B05C 17/01 222/326 |
| 5,197,635 A * | 3/1993 | Chang | ................. | B05C 17/00553 222/137 |
| 5,511,699 A * | 4/1996 | Tepic | ................. | B05C 17/01 222/326 |
| 5,514,135 A | 5/1996 | Earle | | |
| 5,615,807 A * | 4/1997 | Peng | ................. | B05C 17/01 222/153.01 |
| 5,638,997 A * | 6/1997 | Hawkins | ............. | A61B 17/8822 222/327 |
| 6,086,594 A | 7/2000 | Brown | | |
| 6,110,179 A * | 8/2000 | Flivik | ................. | A61B 17/8808 606/94 |

(Continued)

*Primary Examiner* — Zade Coley (57) ABSTRACT

An instrument for performing a medical procedure includes a drive shaft, a holding clutch, a drive clutch, and an actuator. The holding clutch only allows advancement of the drive shaft, while the drive clutch transfers an advancement force from the actuator to the drive shaft. The dual clutch system allows a lever to be used as the actuator so that a user can generate large actuation forces manually (and optionally remotely) without significant physical effort. This capability can beneficially improve the usability and effectiveness of percutaneous surgical systems, such as those for vertebroplasty or kyphoplasty.

19 Claims, 7 Drawing Sheets

(56) References Cited

U.S. PATENT DOCUMENTS

| | | | | |
|---|---|---|---|---|
| 6,286,729 B1* | 9/2001 | Lin | ............... | G01F 11/026 222/326 |
| 6,348,055 B1 | 2/2002 | Preissman | | |
| 6,412,667 B1* | 7/2002 | Huang | ............... | B05C 17/013 222/327 |
| 6,766,923 B1* | 7/2004 | Huang | ............... | B05C 17/01 222/327 |
| 7,008,433 B2 | 3/2006 | Voellmicke et al. | | |
| 7,112,205 B2 | 9/2006 | Carrison | | |
| 7,980,428 B2* | 7/2011 | Beckett | ............... | B05C 17/01 222/391 |
| 2002/0117016 A1* | 8/2002 | Beckett | ............... | B05C 17/01 74/111 |
| 2004/0122438 A1 | 6/2004 | Abrams | | |
| 2005/0070915 A1* | 3/2005 | Mazzuca | ............... | A61B 17/8822 606/93 |
| 2005/0113843 A1* | 5/2005 | Arramon | ............... | A61B 17/8833 606/94 |
| 2005/0180806 A1 | 8/2005 | Green et al. | | |
| 2006/0052794 A1 | 3/2006 | McGill et al. | | |
| 2006/0074433 A1 | 4/2006 | McGill et al. | | |
| 2006/0235417 A1* | 10/2006 | Sala | ............... | A61B 17/8811 606/79 |
| 2006/0264967 A1 | 11/2006 | Ferreyro et al. | | |
| 2006/0266372 A1 | 11/2006 | Miller et al. | | |
| 2007/0027230 A1 | 2/2007 | Beyar et al. | | |
| 2007/0067034 A1* | 3/2007 | Chirico | ............... | A61B 17/70 623/17.11 |
| 2008/0009876 A1* | 1/2008 | Sankaran | ............... | A61B 17/1617 606/84 |
| 2008/0027456 A1 | 1/2008 | Truckai et al. | | |
| 2008/0039856 A1 | 2/2008 | DiMauro et al. | | |
| 2008/0047983 A1* | 2/2008 | Beckett | ............... | B05C 17/01 222/391 |
| 2008/0142551 A1* | 6/2008 | Strobel-Schmidt | ... | B05C 17/012 222/333 |

* cited by examiner

HIGH PRESSURE SURGICAL SYSTEM

CROSS REFERENCE TO RELATED APPLICATIONS

This application is a continuation of U.S. patent application Ser. No. 12/512,929, filed on Jul. 30, 2009, which is incorporated herein by reference, in its entirety.

FIELD OF THE INVENTION

The invention relates to a system and method for performing a surgical procedure, and in particular, to a system for efficiently generating high pressures in a surgical instrument.

BACKGROUND OF THE INVENTION

For many individuals in our aging world population, undiagnosed and/or untreatable bone strength losses have weakened these individuals' bones to a point that even normal daily activities pose a significant threat of fracture. In one common scenario, when the bones of the spine are sufficiently weakened, the compressive forces in the spine can cause fracture and/or deformation of the vertebral bodies. For sufficiently weakened bone, even normal daily activities like walking down steps or carrying groceries can cause a collapse of one or more spinal bones. A fracture of the vertebral body in this manner is typically referred to as a vertebral compression fracture. Other commonly occurring fractures resulting from weakened bones can include hip, wrist, knee and ankle fractures, to name a few.

Fractures such as vertebral compression fractures often result in episodes of pain that are chronic and intense. Aside from the pain caused by the fracture itself, the involvement of the spinal column can result in pinched and/or damaged nerves, causing paralysis, loss of function, and intense pain which radiates throughout the patient's body. Even where nerves are not affected, however, the intense pain associated with all types of fractures is debilitating, resulting in a great deal of stress, impaired mobility and other long-term consequences. For example, progressive spinal fractures can, over time, cause serious deformation of the spine ("kyphosis"), giving an individual a hunched-back appearance, and can also result in significantly reduced lung capacity and increased mortality.

Until recently, treatment options for vertebral compression fractures, as well as other serious fractures arid/or losses in bone strength, were extremely limited—mainly pain management with strong oral or intravenous medications, reduced activity, bracing and/or radiation therapy, all with mediocre results. Because patients with these problems are typically older, and often suffer from various other significant health complications, many of these individuals are unable to tolerate invasive surgery. In addition, to curb further loss of bone strength, many patients are given hormones and/or vitamin/mineral supplements—again with mediocre results and often with significant side effects.

In an effort to more effectively and directly treat vertebral compression fractures, minimally invasive techniques such as vertebroplasty and, subsequently, kyphoplasty, have been developed. Both techniques involves the percutaneous injection of a flowable reinforcing material, usually polymethylmethacrylate (PMMA—commonly known as bone cement), into a fractured, weakened, or diseased vertebral body. Shortly after injection, the liquid filling material hardens or polymerizes, desirably supporting the vertebral body internally, alleviating pain and preventing further collapse of the injected vertebral body.

In a vertebroplasty procedure, a needle is inserted directly into a vertebral body, and the bone cement is dispensed from the needle. Because the liquid bone cement naturally follows the path of least resistance within bone, and because the small-diameter needles used to deliver bone cement in vertebroplasty procedure typically require either high delivery pressures to ensure that the bone cement remains within the already compromised vertebral body is a significant concern in vertebroplasty procedures.

Kyphoplasty addresses this issue by first creating a cavity within the vertebral body (e.g., with an inflatable balloon to enable the procedure to be performed percutaneously) and then filling that cavity with bone filler material. The cavity provides a natural containment region that minimizes the risk of bone filler material escape from the vertebral body. An additional benefit of kyphoplasty is that the creation of the cavity can also restore the original height of the vertebral body, further enhancing the benefit of the procedure.

In both vertebroplasty and kyphoplasty procedures (as in any procedure in which filler material is delivered percutaneously to a target location in a body), the ability to apply higher pressures to the filler material can beneficially enhance the safety, efficacy, and/or flexibility of the procedure. For example, the use of higher viscosity bone cements can reduce the likelihood of extravasation, and the use of smaller diameter delivery tools (e.g., cement delivery needles or nozzles) can minimize trauma to the patient and provide greater placement flexibility.

Accordingly, it is desirable to provide surgical tools and techniques that can generate high pressures for use in surgical procedures.

SUMMARY OF THE INVENTION

By incorporating a lever-actuated drive clutch and a holding clutch into a mechanism for advancing a plunger or piston, high pressures for surgical material delivery can be generated by a surgeon without significant physical exertion.

In one embodiment, a surgical instrument includes a shaft that effectuates the action of the surgical instrument (e.g., drives a plunger in a syringe to dispense a flowable material or deploys a manipulation structure for a body part). A housing for the shaft also includes a holding clutch mounted on the shaft, a drive clutch mounted on the shaft, and a lever for applying a translation force to the drive clutch.

The holding clutch is configured such that it allows advancement of the shaft (i.e., movement of the shaft in a proximal direction relative to the housing), but does not allow movement in the opposite direction (i.e., does not allow retraction of the shaft). The drive clutch is configured such that it exhibits a range of motion relative to the housing, but only engages with the shaft when being driven in the proximal direction by the lever.

Thus, when the lever is actuated, it drives the drive clutch in a proximal direction. The drive clutch engages with the shaft, thereby advancing the shaft as it moves. The holding clutch allows this proximal motion of the shaft, but once the advancement force being applied by the lever is removed, the holding clutch prevents any reverse motion of the shaft (retraction). Meanwhile, the drive clutch disengages from the shaft and returns to its original position within the housing. The lever can then be actuated again to repeat the process and continue to advance the shaft.

In various embodiments, the drive clutch and/or the holding clutch can include binding plates to provide controllable engagement/disengagement capabilities with the shaft. The binding plates can simply comprise plates with apertures slightly larger than the shaft dimensions, such that if either plate is substantially perpendicular to the shaft, the shaft can move freely with respect to the plate, but if the binding plate is canted with respect to the shaft, relative motion between the plate and shaft is prevented. In various embodiments, the binding plates and/or shaft can include features that enhance the binding functionality.

In one embodiment, the holding clutch includes a binding plate and a bias spring, and the drive clutch includes a binding plate and a return spring. The bias spring in the holding clutch causes the binding plate in the holding clutch to assume a normally canted orientation (i.e., engaged) with respect to the shaft, thereby preventing shaft retraction. Advancement of the shaft overcomes the bias spring and presses the binding plate against a surface(s) or feature(s) of the housing that cause the binding plate to become oriented substantially perpendicularly (i.e., disengaged) with respect to the shaft. When the advancement of the shaft ceases, the bias spring returns the binding plate to its canted orientation, thereby locking the shaft in place.

Meanwhile, the return spring in the drive clutch biases the binding plate in the drive clutch towards a perpendicular orientation (disengaged) with respect to the shaft and towards a baseline position within the housing. The binding plate in the drive clutch is further configured to receive off-axis loading from the lever that causes canting (engagement) with respect to the shaft, thereby resulting in any advancement loading from the shaft lever being transferred to the shaft.

Thus, as the lever is actuated to apply an advancement force to the binding plate in the drive clutch, that binding plate engages with the shaft to begin advancing the shaft. The shaft advancement causes the binding plate in the holding clutch to disengage from the shaft to allow further advancement of the shaft. When the lever is released, the advancement of the shaft stops, the binding plate in the holding clutch is re-engaged with the shaft by the bias spring to prevent retraction, and the binding plate in the drive clutch disengages from the shaft and is returned to its baseline position by the return spring. The lever can then be re-actuated to further advance the shaft.

As will be realized by those of skilled in the art, many different embodiments of a surgical instrument, kit, and/or methods of using a surgical instrument incorporating a dual-clutch mechanism for enabling high force generation are possible. Additional uses, advantages, and features of the invention are set forth in the illustrative embodiments discussed in the detailed description herein and will become more apparent to those skilled in the art upon examination of the following.

DETAILED DESCRIPTION

By incorporating a lever-actuated drive clutch and a holding clutch into a mechanism for advancing a plunger or piston, high pressures/forces for surgical procedures can be generated by a surgeon without significant physical exertion.

Figure 1:
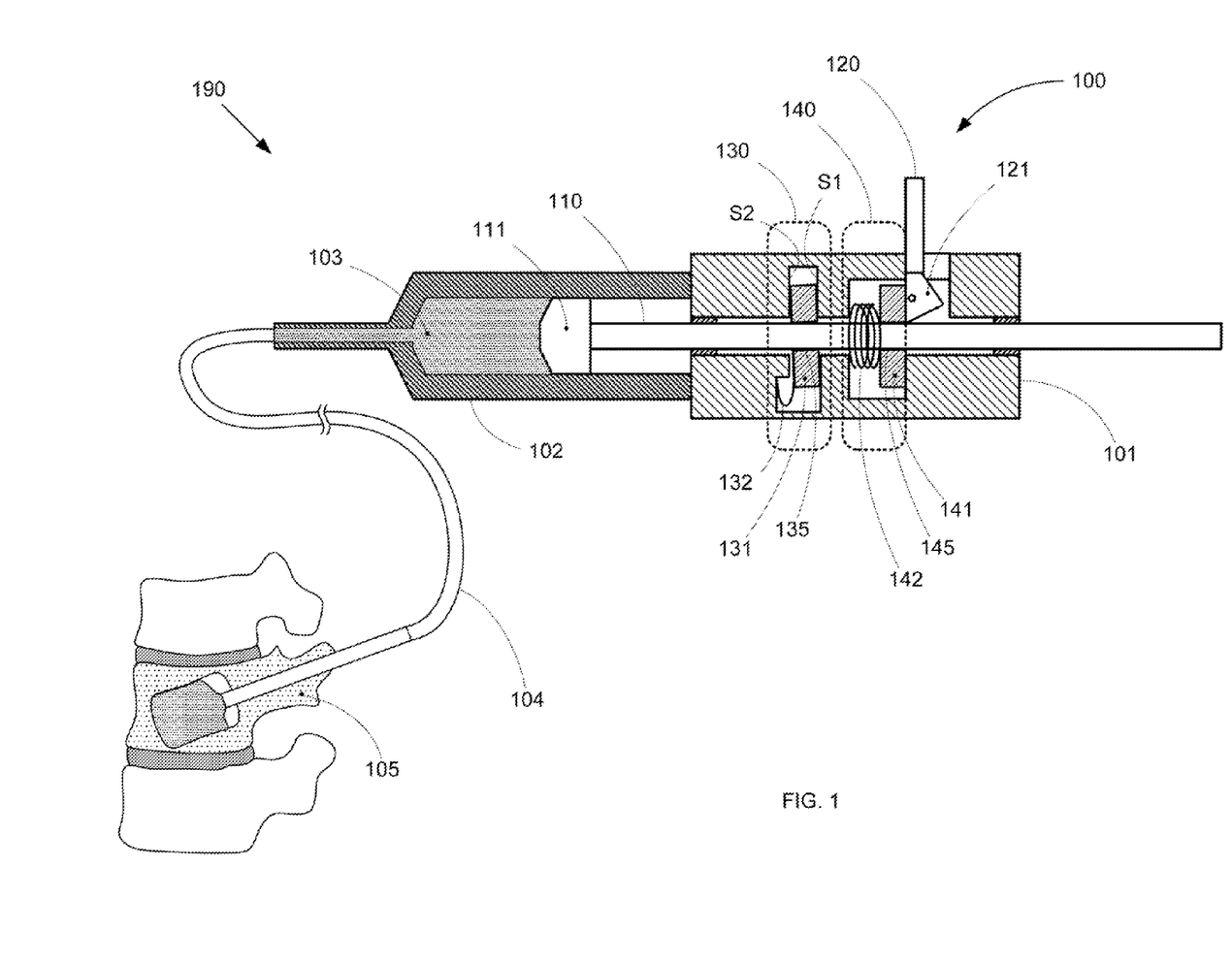
FIG. 1 is a diagram of a surgical instrument that includes a dual clutch system for efficiently generating large internal forces/pressures.

FIG. 1 shows a block diagram of a surgical instrument 190 that includes high force advancement mechanism 100 incorporating a dual-clutch mechanism for applying and maintaining a large force within the surgical instrument. Mechanism 100 includes a housing 101 that houses a holding clutch 130 and a drive clutch 140, both mounted on a shaft 110. Holding clutch 130 and drive clutch 140 enable the advancement of shaft 110 with great force to effectuate the surgical procedure being performed by surgical instrument 190.

Holding clutch 130 can be any mechanism that allows shaft 110 to be moved in one direction and resists motion of shaft 110 in the opposite direction (e.g., a ratchet). Drive clutch 140 can be any mechanism that controllably engages and disengages shaft 110 (e.g., a chuck or clamp, among others). When an actuator such as a lever 120 mounted on housing 101 applies a force to drive clutch 140, drive clutch 140 engages and advances shaft 110. When lever 120 is released, holding clutch 130 maintains the position of shaft 110 while drive clutch 140 disengages from shaft 110 and returns to its original position. In this manner, the force multiplication provided by the action of lever 120 is directly converted to advancement of shaft 110.

For exemplary purposes, surgical instrument 100 is depicted in FIG. 1 as a syringe 102 for performing vertebroplasty or kyphoplasty. A plunger tip 111 at the end of shaft 110 drives bone filler material 103 (e.g., bone cement) from syringe 102 through a delivery path 104 (e.g., a flexible tube and delivery needle/nozzle) into a vertebral body 105. The large force generated by mechanism 100 allows a high viscosity bone filler material 103 to be delivered during the procedure, thereby minimizing extravasation risks.

Figure 1A:
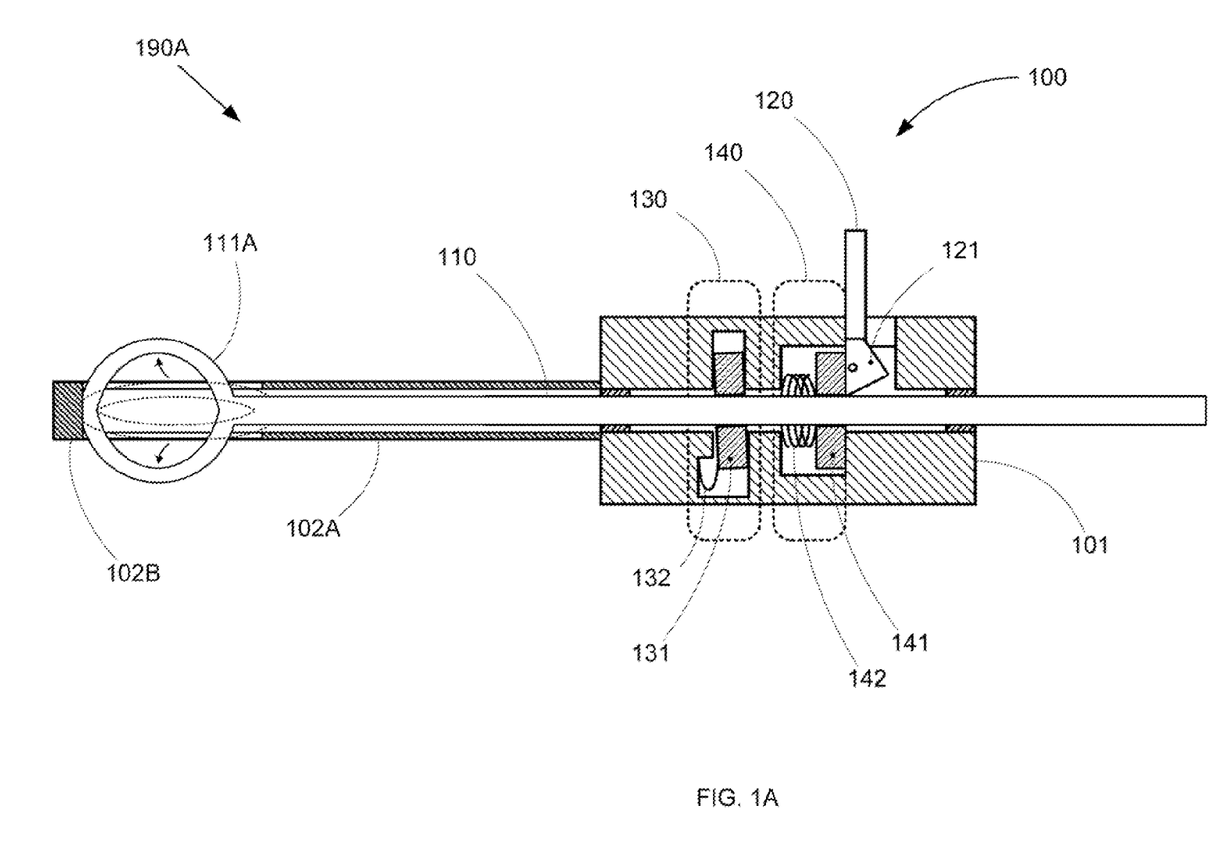
FIG. 1A is a diagram of an alternative surgical instrument incorporating the dual clutch system of FIG. 1.

Note that in various other embodiments, surgical instrument 100 can be any type of surgical system in which the generation of large forces would be beneficial. For example, FIG. 1A shows an alternative embodiment of surgical instrument 100A in which shaft 110 includes an expandable element 111A that can be used for percutaneous bone manipulation (e.g., cavity creation within cancellous bone or restoring vertebral endplate position after a fracture has occurred). As shaft 110 is advanced through a sheath 102A, expandable element 111A is compressed against a solid tip 102B of sheath 102A, and expands outwards in response. The large forces that can be applied to shaft 110 enable the use of a robust expandable element 111A, which in turn can enable more effective bone manipulation during surgical procedures. Various other embodiments of surgical instruments incorporating a dual clutch system will be readily apparent.

Returning to FIG. 1, holding clutch 130 can be any mechanism that allows shaft 110 to be moved in one direction and resists motion of shaft 110 in the opposite direction (e.g., a ratchet or other type of restraining mechanism). Drive clutch 140 can be any mechanism that controllably engages and disengages shaft 110 (e.g., a chuck or clamp, among others). In one embodiment, holding clutch 130 and drive clutch 140 can include binding plates 131 and 141, respectively.

Binding plates 131 and 141 include apertures 135 and 145, respectively, through which shaft 110 is passed. The relative angle of binding plates 131 and 141 relative to shaft 110 determines whether holding clutch 130 and drive clutch 140, respectively, are engaged with or disengaged from shaft 110. For example, when binding plate 131 is substantially perpendicular to shaft 110, holding clutch 130 is disengaged from shaft 110, and shaft 110 can freely move with respect to holding clutch 130. However, when binding plate 131 is sufficiently canted with respect to shaft 110 (i.e., is sufficiently non-parallel to shaft 110), holding clutch 130 is engaged with shaft 110 and no relative motion is possible.

Likewise, when binding plate 141 is substantially perpendicular to shaft 110, drive clutch 140 is disengaged from shaft 110 and can move freely with respect to shaft 110. However, when binding plate 141 is sufficiently canted with respect to shaft 110, drive clutch 140 is engaged with shaft 110, and any force (and motion) applied to drive clutch 140 is also applied to shaft 110.

Note that binding plates 131 and 141, along with shaft 110, can take any configuration that enables the above-described operation wherein canted orientation relative to the shaft results in engagement (binding), and perpendicular orientation relative to the shaft results in disengagement (release). For example, shaft 110 can include grooves, ridges, or other features that enhance engagement with the edges of apertures 135 and 145. Shaft 110 could be round, square, rectangular, or any other shape (e.g., a rectangular shaft 110 within slot-shaped apertures 135 and 145 could provide a larger engagement area when either holding clutch 130 or drive clutch 140 is engaged. Various other embodiments will be readily apparent.

Holding clutch 130 further includes a bias spring 132 that forces binding plate 131 against a surface S1 of housing 101. Surface S1 causes binding plate 131 to orient itself in a canted position relative to shaft 110, thereby engaging shaft 110. In various embodiments, surface S1 can be a continuous surface that is angled with respect to a plane perpendicular to shaft 110, multiple surfaces or features that cause binding plate 131 to align in a non-perpendicular position (with respect to shaft 110), or any other suitably orienting structure. In this manner, bias spring 132 creates a default engaged condition for holding clutch 130 that resists retraction of shaft 110.

Meanwhile, drive clutch 140 further includes a return spring 142 that places binding plate 141 in a perpendicular position relative to shaft 110 and moves binding plate 141 into a baseline position within housing 101. Note that while a single spring is depicted for clarity, return spring 142 can include any number of spring or elastomeric elements that tend to orient binding plate 141 substantially perpendicularly with respect to shaft 110. In this manner, return spring 142 acts to return binding plate 141 back to a default position without requiring motion of shaft 110.

Figure 2:
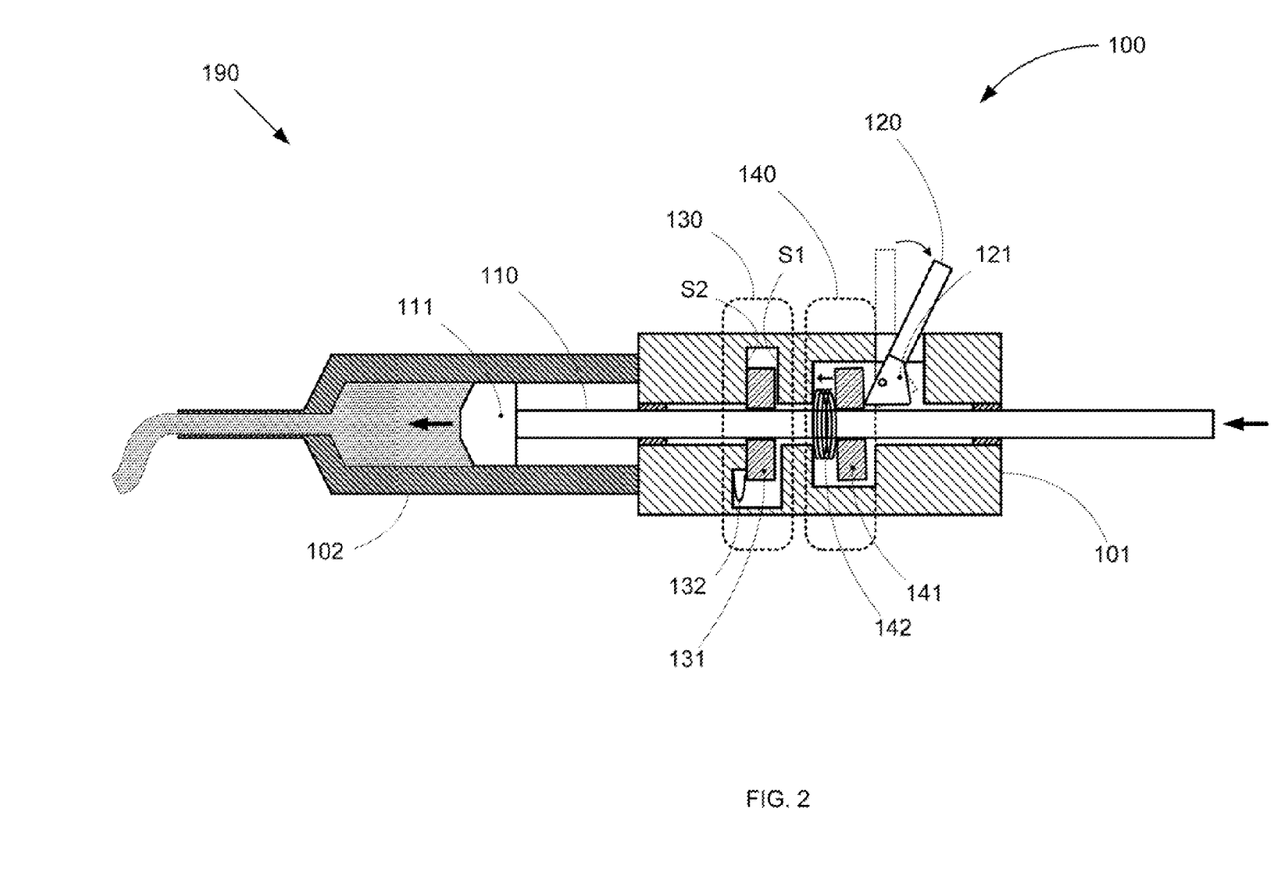
FIGS. 2-3 show an exemplary actuation of the surgical instrument of FIG. 1

To advance shaft 110, lever 120 is rotated rearward (proximally), which causes drive element 121 at the end of lever 120 to push forward (distally) against one portion of binding plate 141, as shown in FIG. 2. Note that although a simple lever is depicted for clarity, in various embodiments, lever 120 can take any shape or any combination of elements. For example, in one embodiment, drive element 121 of lever 120 can be a cam that applies force to the same location on binding plate 141 as lever 120 is rotated. In various other embodiments, lever 120 can incorporate a linkage, geared, or threaded mechanism.

However, regardless of the particular configuration of lever 120, because the force applied by drive element 121 is applied unevenly around aperture 145 (i.e., force is not evenly distributed about aperture 145), actuation causes binding plate 141 to become canted with respect to shaft 110. Consequently, actuation of lever 120 quickly engages binding plate 141 with shaft 110, such that any subsequent force applied to binding plate 141 by drive element 121 is transmitted to shaft 110 as well.

Note that the sensitivity of this binding action can be controlled in various ways, such as increasing the width of binding plate 141 and/or sizing aperture 145 to be only slightly larger than the dimensions of shaft 110 (e.g., dimensioning aperture 145 to provide a slip fit hole for a round shaft 110). Typically, it is desirable to have binding plate 141 quickly engage with shaft 110, although if less engagement sensitivity is desired, the dimensions of aperture 145 could be increased or the width of binding plate 141 could be decreased.

As drive element 121 continues to apply force to binding plate 141 (now engaged with shaft 110), shaft 110 begins to advance (proximally) within housing 101. At the onset of this advancement, binding plate 131 is engaged with shaft 110, and advances along with shaft 110. However, binding plate 131 quickly comes into contact with surface S2 of housing 101. Surface S2 is configured such that it orients binding plate 131 substantially perpendicularly with respect to shaft 110, thereby disengaging binding plate 110 from shaft 110. Note that surface 82 can be a continuous surface, or multiple surfaces or features that cause binding plate 131 to be positioned perpendicularly with respect to shaft 110.

Figure 3:
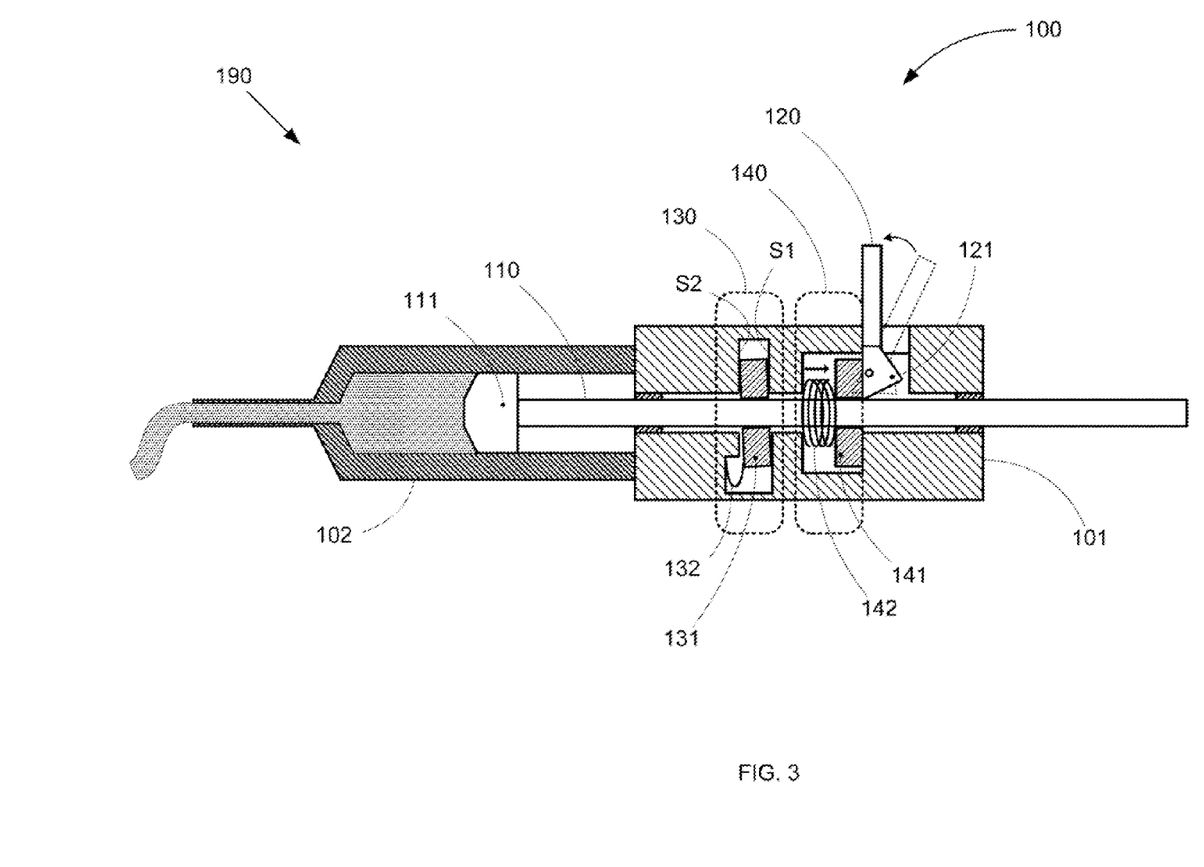

Once binding plate 131 is disengaged from shaft 110, any further loading of binding plate 141 by drive element 121 results in advancement of shaft 110 relative to binding plate 131. Then, as shown in FIG. 3, when lever 120 is released, the advancement of shaft 110 stops, and so bias spring 132 pushes binding plate 131 back against surface S1, thereby re-engaging binding plate 131 with shaft 110 and preventing any retraction (i.e., movement in the proximal direction) of shaft 110. Meanwhile, return spring 142 presses against binding plate 141, orienting binding plate 141 substantially perpendicularly with respect to shaft 110. As a result, binding plate 141 is disengaged from shaft 110 and returned to its base position (along with lever 120).

In this manner, each actuation of lever 120 advances shaft 110 and holds shaft 110 in that new position. The operation described above with respect to FIGS. 1-3 can be repeated to advance shaft 110 a desired distance with respect to housing 101. The force multiplication provided by this lever-based actuation allows shaft 110 to be advanced with significant force compared to the actuation force the user applies to lever 120. Consequently, mechanism 100 can be incorporated into any surgical instrument 190 that would benefit from the ability to generate large internal pressures/forces.

Figure 1B:
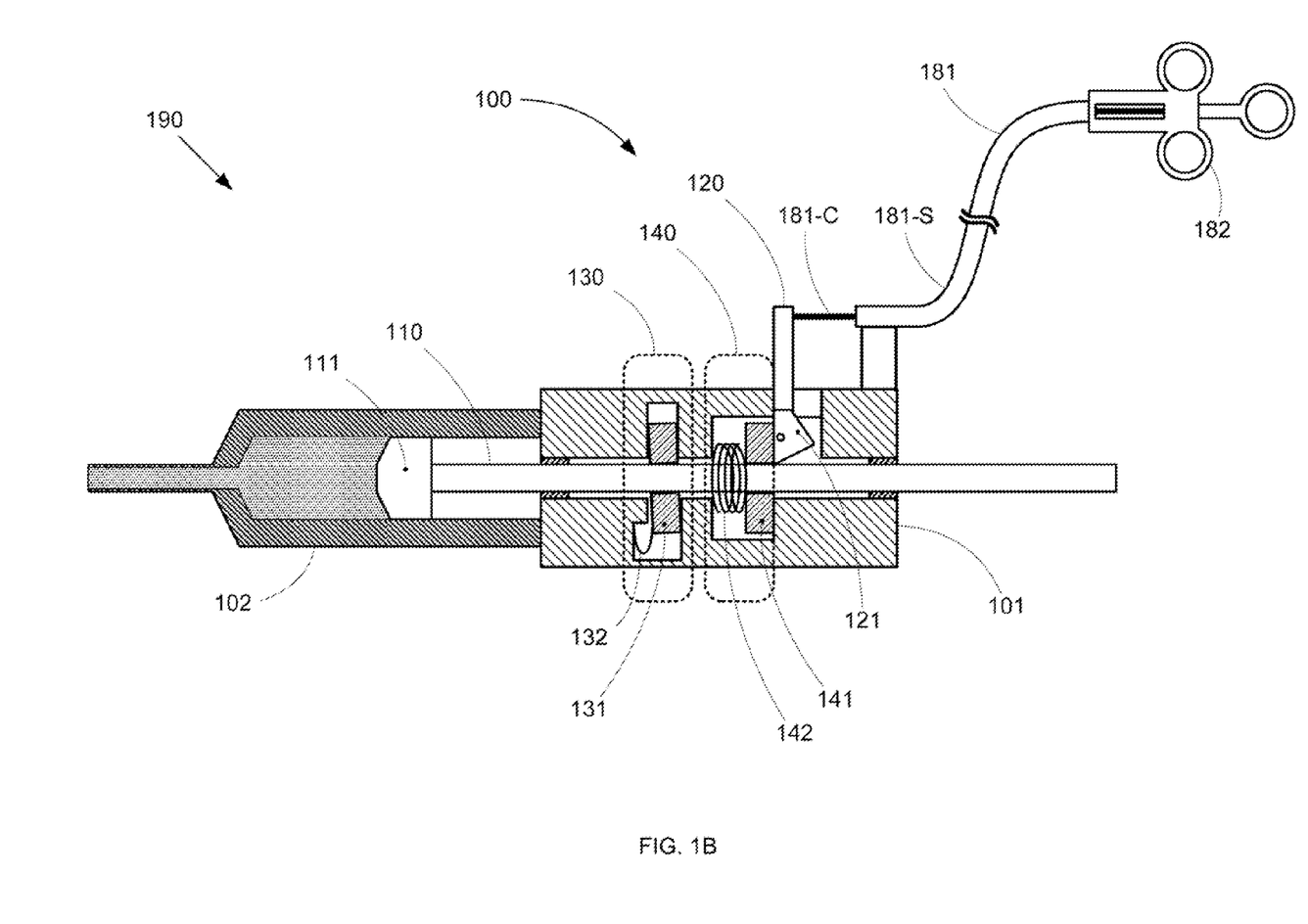
FIG. 1B is a diagram of an alternative surgical instrument that provides remote actuation capabilities in combination with the dual clutch mechanism of FIG. 1.

For example, because lever 120 does not require a large actuation force to produce large advancement forces on shaft 110, mechanism 100 is conducive to remote operation. FIG. 1B shows an embodiment of surgical instrument 190 in which lever 120 is connected to a remote controller 182 by a push-pull cable 181. The sheath (casing) 181-S of push-pull cable 181 is connected to housing 101, and core 181-C of push-pull cable 181 is connected to lever 120. Controller 182 can move core 181-C relative to sheath 181-3, thereby allowing lever 120 to be actuated remotely from surgical instrument 190. This in turn, can beneficially allow the user to be removed from any radiation field in which surgical instrument 190 is being used. Various other remote operation mechanisms will be readily apparent, such as flexible cable-based, solenoid-based, motor-based, and pulley-based mechanisms, among others.

Figure 4:
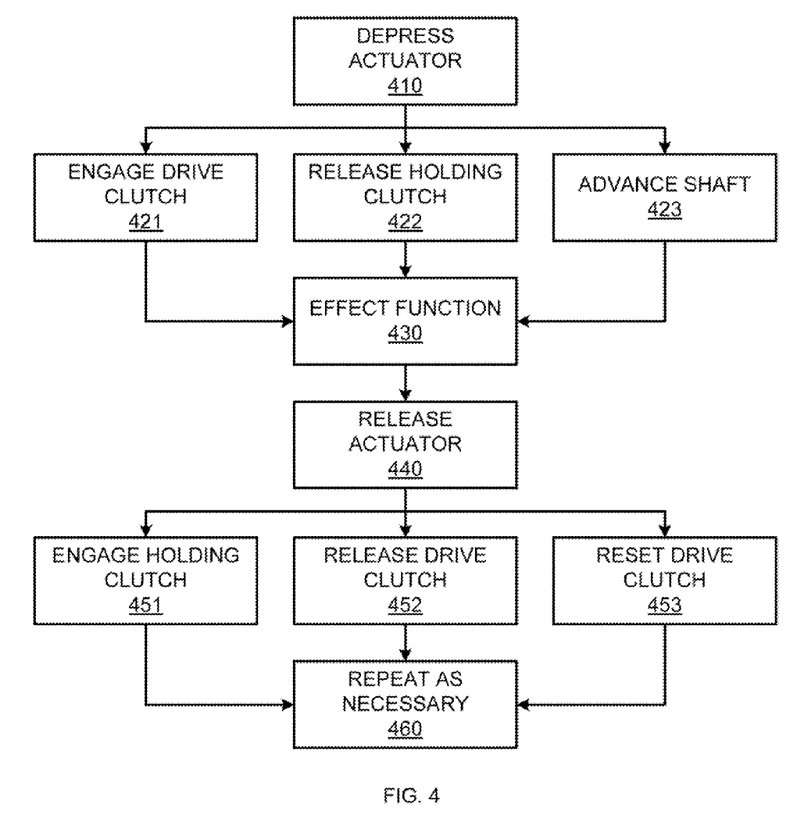
FIG. 4 is a flow diagram for the use of the surgical instrument of FIG. 1

FIG. 4 shows a flow diagram of the mechanical operation described above with respect to FIGS. 1-3. In a DEPRESS ACTUATOR step 410, an actuation mechanism (e.g., lever 120) is actuated. In response, in an ENGAGE DRIVE CLUTCH step 421, a first clutch engages a drive shaft of a surgical instrument (e.g., binding plate 141 of drive clutch 140 being canted with respect to shaft 110). Roughly concurrently, in a RELEASE HOLDING CLUTCH step 422, a second clutch is disengaged from the drive shaft (e.g., binding plate 131 of holding clutch 130 coming in to contact with surface S2 and being oriented substantially perpendicularly to drive shaft 110), and in an ADVANCE SHAFT step 423, the drive shaft is advanced (i.e., moved proximally) in response to a drive force applied to the second clutch (e.g., drive element 121 continuing to apply force to binding plate 141). The shaft movement enables performance of a desired surgical procedure (e.g., delivery of bone filler material 103 as shown in FIGS. 1-3, or the expansion of a cavity creation device for bone such as expandable element 111A shown in FIG. 1A) in an EFFECT FUNCTION step 430.

Then, the actuation mechanism is released in a RELEASE ACTUATOR step 440, which causes the second clutch to re-engage with the drive shaft in an ENGAGE HOLDING CLUTCH step 451, while disengaging the first clutch from the drive shaft in a RELEASE DRIVE CLUTCH step 452, and returning the first clutch to a baseline position (e.g., return spring 142 pushing binding plate 141 back to its baseline position) in a RESET DRIVE CLUTCH step 453. Finally, in a REPEAT AS NECESSARY step 460, the sequence of steps 410-453 is repeated until the a desired amount of drive shaft advancement and/or force exertion by the drive shaft is reached (e.g., a desired amount of bone filler material 103 is dispensed at a desired pressure or an expandable element 111A is expanded to a desired size or applies a desired pressure on surrounding bone).

Note that while steps 421-423 and steps 451-453 are described as occurring relatively concurrently for explanatory purposes, in various other embodiments, steps 421-423 can occur in any sequence, as can steps 451-453. For example, as described above with respect to FIGS. 1-3, binding plate 141 engages shaft 110 (step 421) and begins to advance shaft 110 (step 423) slightly before binding plate 131 disengages from shaft 110 (step 422). However, various other embodiments of drive clutch 140 and holding clutch 130 may produce a slightly different ordering of steps 421-423 and 451-453.

Figure 5:
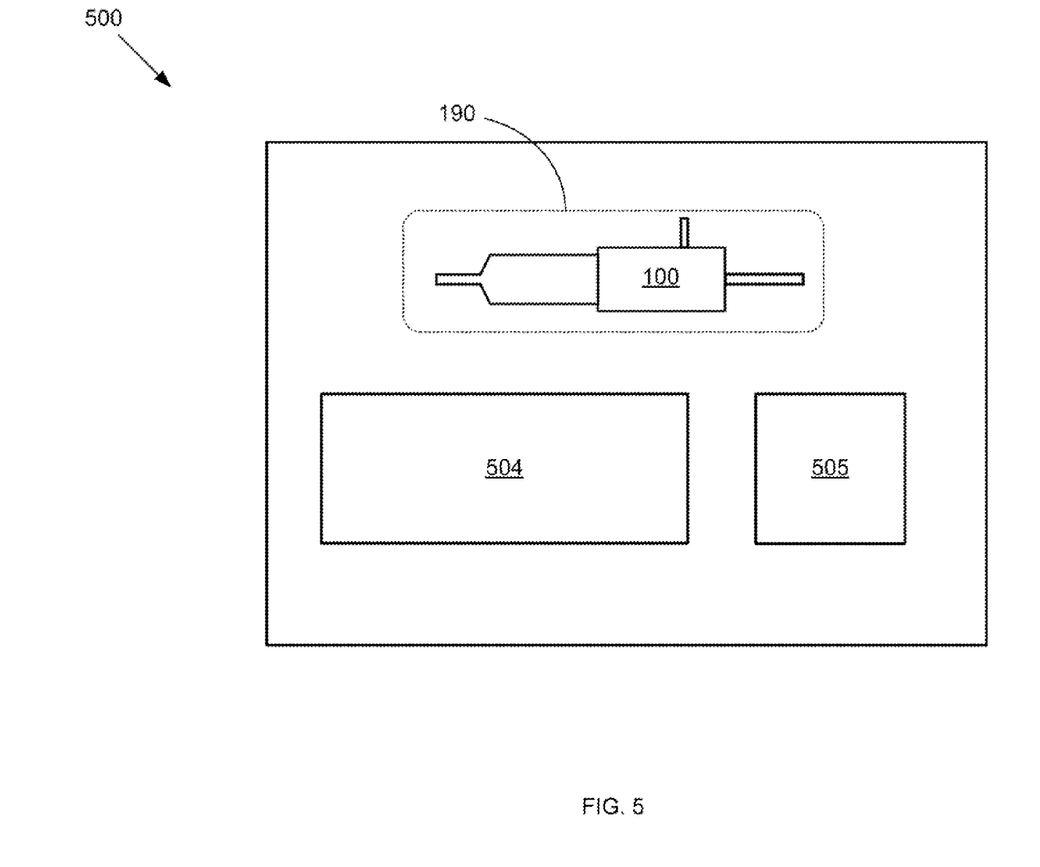
FIG. 5 is a block diagram of a kit that includes the surgical instrument of FIG. 1.

FIG. 5 shows a diagram of a kit 500 for use in performing a surgical procedure. Kit 500 includes a surgical instrument 190 (e.g., surgical instrument 190 or 190A as shown in FIGS. 1 and 1A, respectively) that includes a high force advancement mechanism 100 (as described with respect to FIGS. 1-3). Kit 500 further includes optional additional instruments 504 and optional directions for use 505 that provide instructions for using surgical instrument 190 and optional additional instruments 504 (e.g., instructions for performing a vertebroplasty or kyphoplasty procedure using surgical instrument 190 and optional additional instruments 504).

For example, kit 500 could be a kit for use in a kyphoplasty procedure, and surgical instrument 190 could be a system for delivering bone filler material (e.g., as described with respect to FIGS. 1-3), in which case optional additional instruments 504 could be tools for creating a void in cancellous bone. Alternatively, kit 500 could be a kit for use in a kyphoplasty procedure in which surgical instrument 190 is a cavity creation system (e.g., as described with respect to FIG. 1A), in which case optional additional instruments 504 could be tools for delivering bone filler material to the void created by surgical instrument 190. Various other additional instruments 504 will be readily apparent for various other surgical procedures.

While various embodiments of the invention have been described above, it should be understood that they have been presented by way of example only, and not limitation, Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain steps may be performed concurrently in a parallel process when possible, as well as performed sequentially as described above. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

The invention claimed is:

1. A surgical instrument, comprising:
    a housing comprising an inner surface defining a cavity,
        a distal end of the housing comprising an opening that is in communication with the cavity;
    a shaft extending through a proximal end of the housing, the shaft comprising a distal end that defines a plunger that is disposed in the cavity;
    a first plate positioned within the cavity and comprising a first aperture, the shaft extending through the first aperture;
    a second plate positioned within the cavity and comprising a second aperture, the shaft extending through the second aperture; and
    a bias spring that engages the second plate to bias the second plate to a resting position in which the second plate is canted relative to the shaft such that the shaft engages the second plate, wherein the second plate moves from the resting position to an actuated position by moving the second plate distally within the cavity until the second plate engages a surface of the housing that extends perpendicular to the shaft such that the second plate extends perpendicular to the shaft to space the second plate apart from the shaft,
    wherein the shaft is movable between a first position in which the plates engage the shaft and the plunger is spaced apart a first distance from the opening and a second position in which the shaft is fixed relative to the first plate and is spaced apart from the second plate and the plunger is spaced apart a second distance from the opening that is less than the first distance.

2. A surgical instrument as recited in claim 1, wherein:
    the plates are canted with respect to shaft when the shaft is in the first position such that the shaft is fixed relative to the plates; and
    the first plate is canted with respect to the shaft and the second plate extends perpendicular to the shaft when the shaft is in the second position such that the shaft is movable relative to the housing.

3. A surgical instrument as recited in claim 1, wherein the shaft is fixed relative to the second plate when the shaft is in the first position and is movable relative to the second plate when the shaft is in the second position.

4. A surgical instrument as recited in claim 1, wherein the shaft is movable from the second position to a third position in which the first plate is canted with respect to the shaft to fix the shaft relative to the first plate and the second plate extends perpendicular to the shaft such that the shaft is movable relative to the second plate.

5. A surgical instrument as recited in claim 4, wherein the shaft is movable from the third position to the first position.

6. A surgical instrument as recited in claim 1, further comprising a return spring that engages the first plate to bias the first plate to a resting position in which the first plate extends perpendicular to the shaft and the shaft is spaced apart from the first plate.

7. A surgical instrument as recited in claim 6, further comprising an actuator that is pivotable relative to the housing and configured to apply a force unevenly around the first aperture to move the first plate from the resting position of the first plate to an actuating position in which the first plate is canted with respect to the shaft to fix the shaft relative to the first plate.

8. A surgical instrument as recited in claim 6, wherein the shaft extends along a longitudinal axis between the distal end of the shaft and an opposite proximal end of the shaft, the return spring being coaxial with the longitudinal axis.

9. A surgical instrument as recited in claim 1, wherein the shaft extends along a longitudinal axis between the distal end of the shaft and an opposite proximal end of the shaft, the bias spring being offset from the longitudinal axis.

10. A surgical instrument, comprising:
a housing comprising an inner surface defining a cavity;
a sheath coupled to the housing, the sheath comprising a distal end having a solid tip and an inner surface defining a passageway that is in communication with the cavity;
a shaft extending through the cavity and into the passageway such that an expandable element of the shaft contacts the solid tip;
a first plate positioned within the housing and comprising a first aperture, the drive shaft extending through the first aperture;
a second plate positioned within the housing and comprising a second aperture, the drive shaft extending through the second aperture; and
a bias spring that engages the second plate to bias the second plate to a resting position in which the second plate is canted relative to the shaft such that the shaft engages the second plate, wherein the second plate moves from the resting position to an actuated position by moving the second plate distally within the cavity until the second plate engages a surface of the housing that extends perpendicular to the shaft such that the second plate extends perpendicular to the shaft to space the second plate apart from the shaft,
wherein the shaft is movable between a first position in which the plates engage the shaft and the expandable element has a first maximum width and a second position in which the shaft is fixed relative to the first plate and is spaced apart from the second plate and the expandable element has an increased second maximum width.

11. A surgical instrument as recited in claim 10, wherein:
the plates are canted with respect to shaft when the shaft is in the first position such that the shaft is fixed relative to the plates; and
the first plate is canted with respect to the shaft and the second plate extends perpendicular to the shaft when the shaft is in the second position such that the shaft is movable relative to the housing.

12. A surgical instrument as recited in claim 10, wherein the shaft is fixed relative to the second plate when the shaft is in the first position and is movable relative to the second plate when the shaft is in the second position.

13. A surgical instrument as recited in claim 10, wherein the shaft is movable from the second position to a third position in which the first plate is canted with respect to the shaft to fix the shaft relative to the first plate and the second plate extends perpendicular to the shaft such that the shaft is movable relative to the second plate.

14. A surgical instrument as recited in claim 13, wherein the shaft is movable from the third position to the first position.

15. A surgical instrument as recited in claim 10, further comprising a return spring that engages the first plate to bias the first plate to a resting position in which the first plate extends perpendicular to the shaft and the shaft is spaced apart from the first plate.

16. A surgical instrument as recited in claim 15, further comprising an actuator that is pivotable relative to the housing and configured to apply a force unevenly around the first aperture to move the first plate from the resting position of the first plate to an actuating position in which the first plate is canted with respect to the shaft to fix the shaft relative to the first plate.

17. A surgical instrument, comprising:
a housing comprising an inner surface defining a cavity, a distal end of the housing comprising an opening that is in communication with the cavity;
a shaft extending through a proximal end of the housing, the shaft comprising a distal end that defines a plunger that is disposed in the cavity;
a first plate positioned within the cavity and comprising a first aperture, the shaft extending through the first aperture;
a second plate positioned within the cavity and comprising a second aperture, the shaft extending through the second aperture; and
a bias spring that engages the second plate to bias the second plate to a resting position in which the second plate is canted relative to the shaft such that the shaft engages the second plate,
wherein the second plate moves from the resting position to an actuated position by moving the second plate distally within the cavity until the second plate engages a surface of the housing that extends perpendicular to the shaft such that the second plate extends perpendicular to the shaft to space the second plate apart from the shaft; and wherein the shaft is movable between a first position in which the plates engage the shaft and a second position in which the shaft is fixed relative to the first plate and is spaced apart from the second plate.

18. A surgical instrument as recited in claim 17, wherein:
the plates are canted with respect to shaft when the shaft is in the first position such that the shaft is fixed relative to the plates; and
the first plate is canted with respect to the shaft and the second plate extends perpendicular to the shaft when the shaft is in the second position such that the shaft is movable relative to the housing.

19. A surgical instrument as recited in claim 17, wherein the shaft is fixed relative to the second plate when the shaft is in the first position and is movable relative to the second plate when the shaft is in the second position.

* * * * *

UNITED STATES PATENT AND TRADEMARK OFFICE
CERTIFICATE OF CORRECTION

PATENT NO.         : 9,579,138 B2
APPLICATION NO.    : 14/645485
DATED              : February 28, 2017
INVENTOR(S)        : Click et al.

Page 1 of 1

It is certified that error appears in the above-identified patent and that said Letters Patent is hereby corrected as shown below:

On the Title Page

In Item (71), under "Applicant", in Column 1, Line 1, delete "SARL, Neuchatel" and insert -- SÀRL, Neuchâtel --, therefor.

In the Specification

In Column 1, Line 7, delete "2009," and insert -- 2009, now Pat. No. 9,005,209, --, therefor.

In Column 1, Line 8, delete "reference," and insert -- reference --, therefor.

In Column 1, Line 49, delete "arid/or" and insert -- and/or --, therefor.

In Column 1, Line 63, delete "involves the" and insert -- involve the --, therefor.

In Column 3, Line 67, delete "FIG. 1" and insert -- FIG. 1. --, therefor.

In Column 4, Line 2, delete "FIG. 1" and insert -- FIG. 1. --, therefor.

In Column 6, Line 31, delete "surface 82" and insert -- surface S2 --, therefor.

In Column 6, Line 66, delete "sheath 181-3," and insert -- sheath 181-S, --, therefor.

In Column 8, Line 13, delete "limitation," and insert -- limitation. --, therefor.

Signed and Sealed this
Fifth Day of September, 2017

Joseph Matal
*Performing the Functions and Duties of the
Under Secretary of Commerce for Intellectual Property and
Director of the United States Patent and Trademark Office*